United States Patent
Hayashi et al.

(10) Patent No.: US 11,523,783 B2
(45) Date of Patent: Dec. 13, 2022

(54) RADIATION DETECTOR MODULE, RADIATION DETECTOR, AND RADIOGRAPHIC IMAGING APPARATUS

(71) Applicant: Hitachi, Ltd., Tokyo (JP)

(72) Inventors: Tatsuhiko Hayashi, Tokyo (JP); Takafumi Ishitsu, Tokyo (JP); Masafumi Onouchi, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 0 days.

(21) Appl. No.: 17/230,015

(22) Filed: Apr. 14, 2021

(65) Prior Publication Data

US 2022/0054098 A1 Feb. 24, 2022

(30) Foreign Application Priority Data

Aug. 24, 2020 (JP) .............................. JP2020-140912

(51) Int. Cl.
*A61B 6/00* (2006.01)
*G01T 1/20* (2006.01)

(52) U.S. Cl.
CPC .......... *A61B 6/4208* (2013.01); *G01T 1/2018* (2013.01)

(58) Field of Classification Search
None
See application file for complete search history.

(56) References Cited

U.S. PATENT DOCUMENTS

| 10,488,532 B2* | 11/2019 | Abenaim ............. G01T 1/2018 |
| 2002/0054659 A1* | 5/2002 | Okumura ............... A61B 6/032 378/19 |
| 2008/0068815 A1* | 3/2008 | Astley ................... A61B 6/032 361/760 |
| 2008/0165921 A1* | 7/2008 | Tkaczyk ................ A61B 6/032 250/366 |
| 2012/0069956 A1* | 3/2012 | Guery .................. G01N 23/046 378/19 |
| 2012/0133054 A1* | 5/2012 | Tkaczyk ................ G01T 1/243 438/57 |

FOREIGN PATENT DOCUMENTS

JP 2003-066149 A 3/2003

\* cited by examiner

*Primary Examiner* — Edwin C Gunberg
(74) *Attorney, Agent, or Firm* — Mattingly & Malur, PC

(57) ABSTRACT

There are provided a radiation detector module, a radiation detector, and a radiographic imaging apparatus which make it possible to increase the row number while suppressing a length in a body-axis direction. The radiation detector module includes a detector substrate on which a scintillator, a photodiode, and AD conversion chips are loaded, and a control substrate which supplies power to the detector substrate and controls the operation of an AD conversion unit (AFE) of each AD conversion chip of the detector substrate. The plurality of radiation detector modules configure a radiation detector which suppresses the length in the body-axis direction by connecting together the two substrates so as to form a two-stage structure by stacking connectors.

14 Claims, 17 Drawing Sheets

A-A SECTION

A-A' SECTION

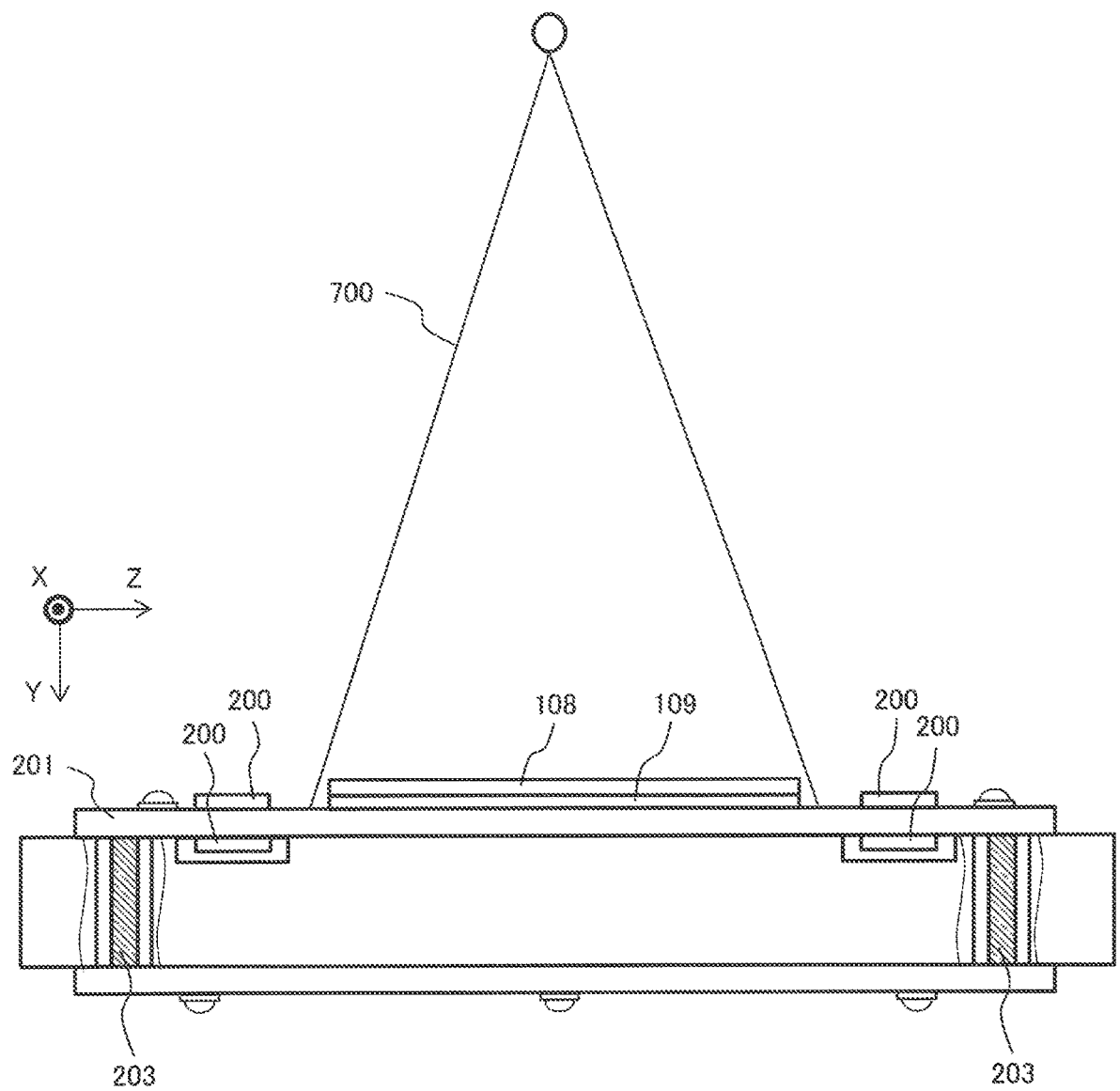

AD CONVERSION CHIP 200 IS NOT ILLUSTRATED

RADIATION DETECTOR MODULE, RADIATION DETECTOR, AND RADIOGRAPHIC IMAGING APPARATUS

CLAIM OF PRIORITY

The present application claims priority from Japanese patent application JP 2020-140912 filed on Aug. 24, 2020, the content of which is hereby incorporated by reference into this application.

BACKGROUND OF THE INVENTION

The present invention pertains to a radiation detecting technology and relates to a radiation detector module, a radiation detector, and a radiographic imaging apparatus which includes the radiation detector.

Nowadays, a multi-slice type radiation detector which makes wide-range imaging possible in a short period of time is mainstream. In the multi-slice type radiation detector, it is requested to increase the row number. However, on the other hand, there is such a problem that it becomes difficult to take an analog signal out of a photodiode with an increase of the row number. Accordingly, in Japanese Unexamined Patent Application Publication No. 2003-66149, there is disclosed a technology of realizing an increase in row number by loading a scintillator, a photodiode, and an AD conversion chip on the same substrate so as to facilitate connection of an analog signal line from the photodiode to an AFE (Analog Font End) which is an AD conversion unit.

SUMMARY OF THE INVENTION

In hospital facilities, there are cases where an increase in size of an X-ray CT (Computed Tomography) apparatus which is the radiographic imaging apparatus induces such a problem that it becomes difficult to install the X-ray CT apparatus in a CT room. In the radiation detector module, in a case where the scintillator, the photodiode, and the AFE are loaded on the same substrate and then also a function of supplying power to the AFE and of controlling the operation of the AFE is added to that substrate, such a problem occurs that the size of the substrate is increased, resulting in an increased length of the radiation detector in a body-axis direction. A further increase in row number of the multi-slice type radiation detector which makes wide-range imaging possible in the short period of time is requested and, on the other hand, length suppression of the radiation detector in the body-axis direction becomes a problem to be solved.

The present invention aims to provide a radiation detector module, a radiation detector, and a radiographic imaging apparatus which solve the abovementioned problems and make it possible to increase the row number while suppressing the length of the radiation detector in the body-axis direction.

According to one aspect of the present invention, there is provided a radiation detector module which includes a detector substrate on which a scintillator which converts X-rays which are incident upon the scintillator from the front-face side to light, a photodiode which converts the light which is converted from the X-rays to an analog signal and AD conversion chips each of which amplifies the analog signal and converts the analog signal to a digital signal are loaded, and a control substrate which supplies power to the detector substrate and controls the operation of an AD conversion unit (AFE) of each AD conversion chip, and in which the two substrates are connected together by stacking connectors so as to form a two-stage structure and a support structure is installed between the substrates.

According to another aspect of the present invention, there is provided a radiation detector which includes a plurality of radiation detector modules, and the support structure is thermally coupled to a radiation detector housing unit to which the plurality of radiation detector modules are attached.

According to further another aspect of the present invention, there is provided a radiographic imaging apparatus which includes a scanner which has a radiation detector therein, a signal processing unit which processes an output signal from the radiation detector and an image generation unit which generates an image signal from the output signal which is processed by the signal processing unit.

According to the present invention, it becomes possible to suppress the length of the radiation detector in the body-axis direction while increasing the row number of the radiation detector.

BRIEF DESCRIPTION OF THE DRAWINGS

FIG. 7 is a diagram illustrating one example that AD conversion chips and the stacking connectors are disposed outside an X-ray irradiation field in the radiation detector module according to a third embodiment of the present invention;

DETAILED DESCRIPTION OF THE PREFERRED EMBODIMENTS

In the following, embodiments of the present invention will be described sequentially by using the drawings.

Figure 1:
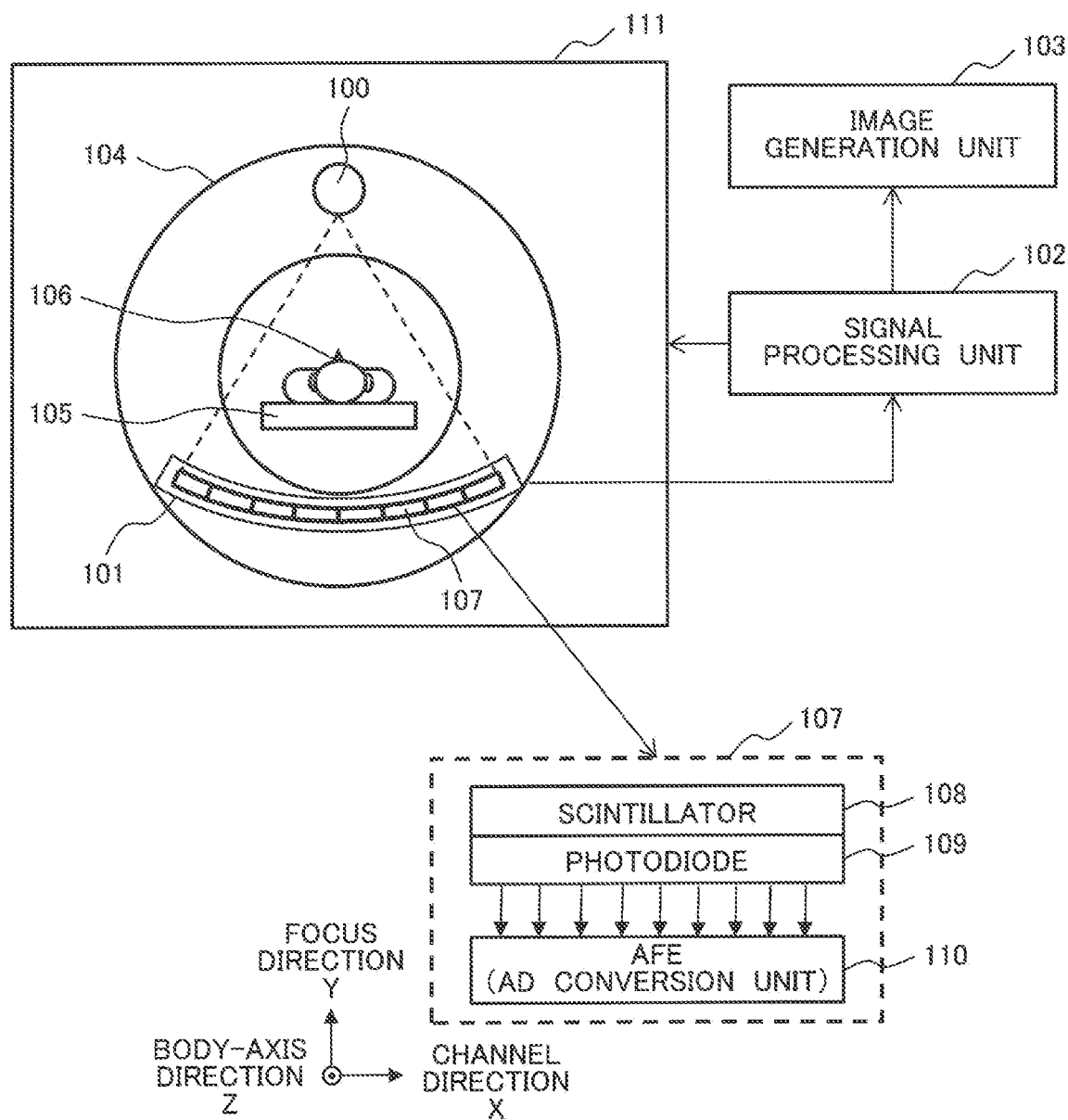
FIG. 1 is a diagram illustrating one example of a gantry of a radiographic imaging apparatus.

As illustrated in FIG. 1, a radiographic imaging apparatus which pertains to the present invention includes an X-ray source 100 which radiates X-rays, a radiation detector 101 which detects the radiated X-rays, a signal processing unit 102 which performs processing such as correction and so forth on an output signal which is detected by the radiation detector 101 and controls operations of a scanner and so forth, and an image generation unit 103 which generates an image of a subject 106 by using a signal which is corrected. The X-ray source 100 and the radiation detector 101 are fixed to a turntable 104 so as to mutually face and is configured to rotate around the subject 106 who lies on a bed 105. In addition, the X-ray source 100, the radiation detector 101, and the turntable 104 are also called a scanner 111 inclusively.

The radiation detector 101 loads a plurality of radiation detector modules 107 thereon and the respective radiation detector modules 107 are attached so as to face a focusing direction (a Y-axis direction) respectively. Each radiation detector module 107 is configured by a scintillator 108 which converts the X-rays to light, a photodiode 109 which converts the light to an analog electric signal, and an AFE (Analog Front End) 110 which is an AD conversion unit which amplifies the analog electric signal and converts the amplified analog electric signal to a digital signal.

First Embodiment

Next, the radiation detector module 107 according to the first embodiment of the present invention will be described by using FIG. 2A to FIG. 2E.

According to the first embodiment, the radiation detector module 107 is configured by a detector substrate 201 on which the scintillator 108 which converts the X-rays to the light, the photodiode 109 which converts the light to the analog electric signal, and a plurality of AD conversion chips 200 each of which serves to amplify the analog electric signal and to convert the amplified analog electric signal to the digital signal are loaded, a control substrate 202 which supplies power to the AFE 110 and controls the operation of the AFE 110, stacking connectors 203 which connect the two substrates 201 and 202 together, and a support structure 204 which is disposed between the detector substrate 201 and the control substrate 202 and fixes the substrates 201 and 202 together.

It becomes possible to suppress a length in a body-axis direction (a Z-axis direction) by dividing the radiation detector module 107 into the detector substrate 201 and the control substrate 202 and thereby forming the two substrates 201 and 202 into a two-stage structure which is disposed in the Y-axis direction. In addition, a metal which is large in elastic coefficient such as aluminum and so forth is used as the material of the support structure 204 which fixes together the substrates 201 and 202 and thereby it becomes possible to increase rigidity of the detector substrate 201 and the control substrate 202. Further, the support structure 204 absorbs heat which is generated from the detector substrate 201 and radiates the heat to the outside.

Here, the analog signal which is output from the photodiode 109 is converted to the digital signal by each AD conversion chip 200, and the digital signal is transferred to the control substrate 202 via each stacking connector 203.

Therefore, each AD conversion chip 200 may be disposed between the photodiode 109 and each stacking connector 203 on the detector substrate 201, and fixing screws 205 of the detector substrate 201 may be disposed on the outer sides of the photodiode 109.

Figure 2A:
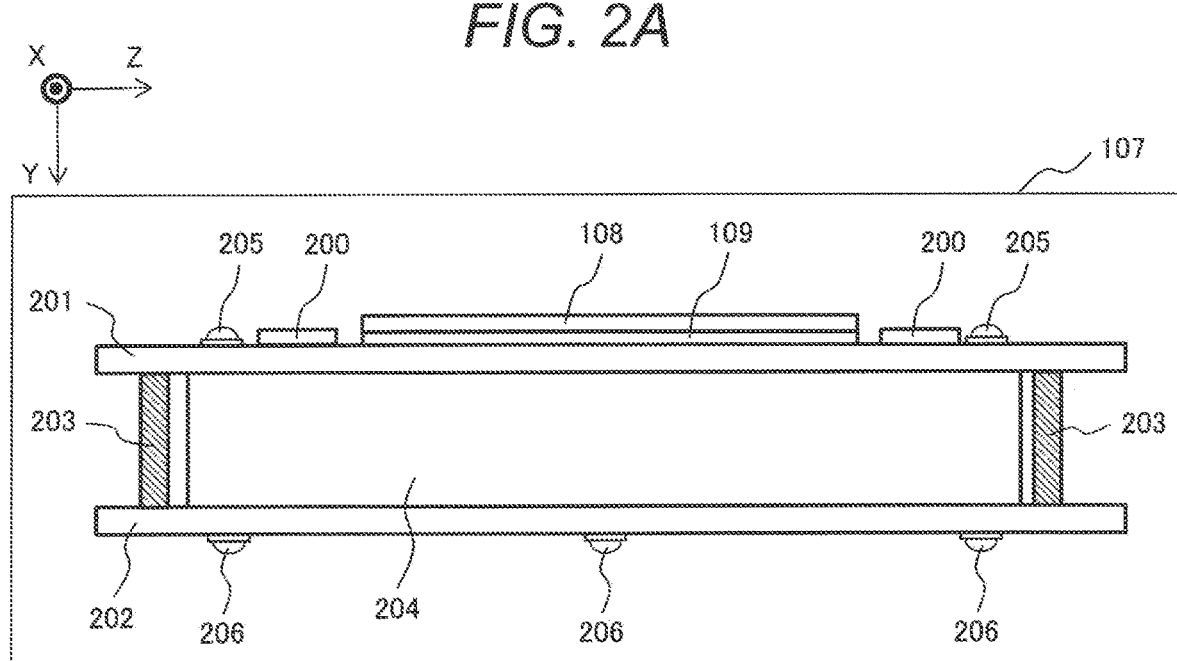
FIG. 2A is a diagram illustrating one example of a configuration of a radiation detector module according to a first embodiment of the present invention.
Figure 2B:
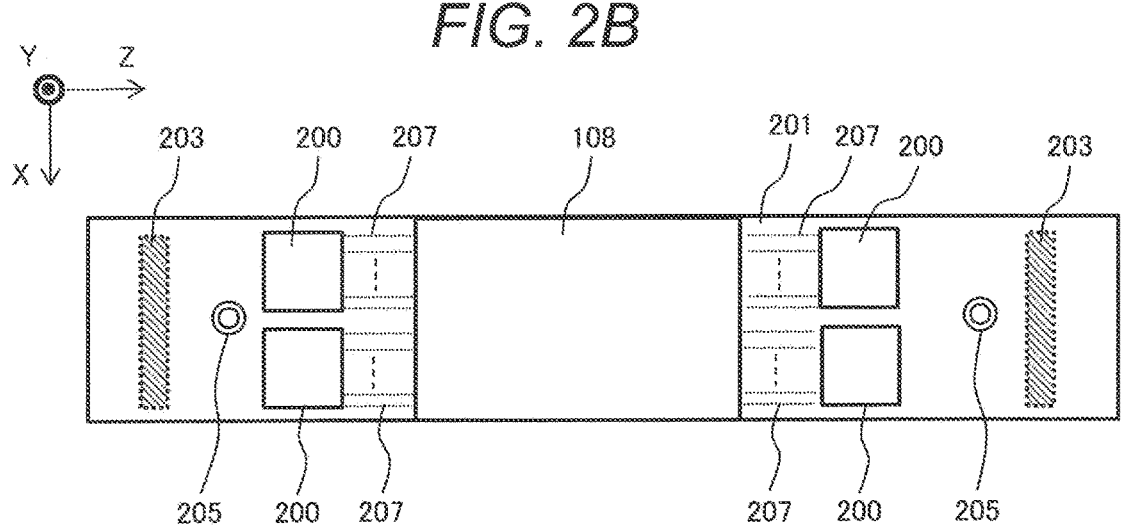
FIG. 2B is a diagram illustrating one example of the configuration of the radiation detector module according to the first embodiment.
Figure 2C:
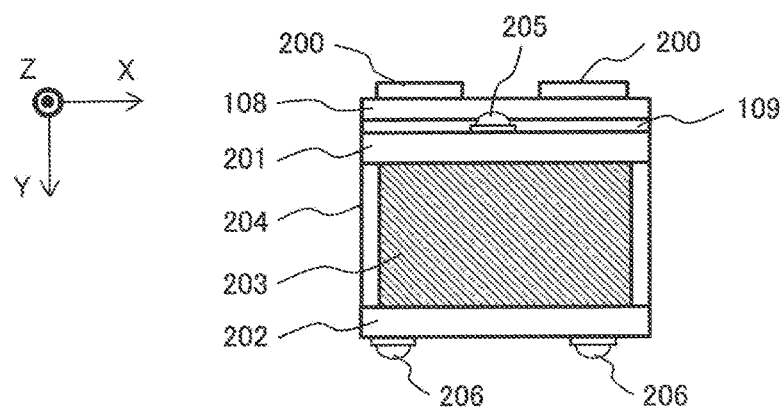
FIG. 2C is a diagram illustrating one example of the configuration of the radiation detector module according to the first embodiment.

For example, as illustrated in FIG. 2A and FIG. 2B, respective elements may be disposed in the Z-axis direction in the order of the fixing screw 205—the AD conversion chip 200—the photodiode 109—the AD conversion chip 200—the fixing screw 205 and may also be disposed in the order of the AD conversion chip 200—the fixing screw 205—the photodiode 109—the fixing screw 205—the AD conversion chip 200. In the former disposition, such an effect that an analog wiring region is not damaged by a screw hole is obtained. In the latter disposition, such an effect that it becomes possible to reduce the Z-axis direction size of the radiation detector 101 is obtained. In addition, the control substrate 202 is fixed to the support structure 204 with screws 206.

Further, as illustrated in FIG. 2B, in a case where analog signals 207 which are output from the photodiode 109 are taken out from the both sides in the body-axis direction (the Z-axis direction), the AD conversion chips 200 on the detector substrate 201 and the stacking connectors 203 which connect the detector substrate 201 with the control substrate 202 are dividedly disposed on the both sides respectively in the body-axis direction (the Z-axis direction).

Figure 2D:
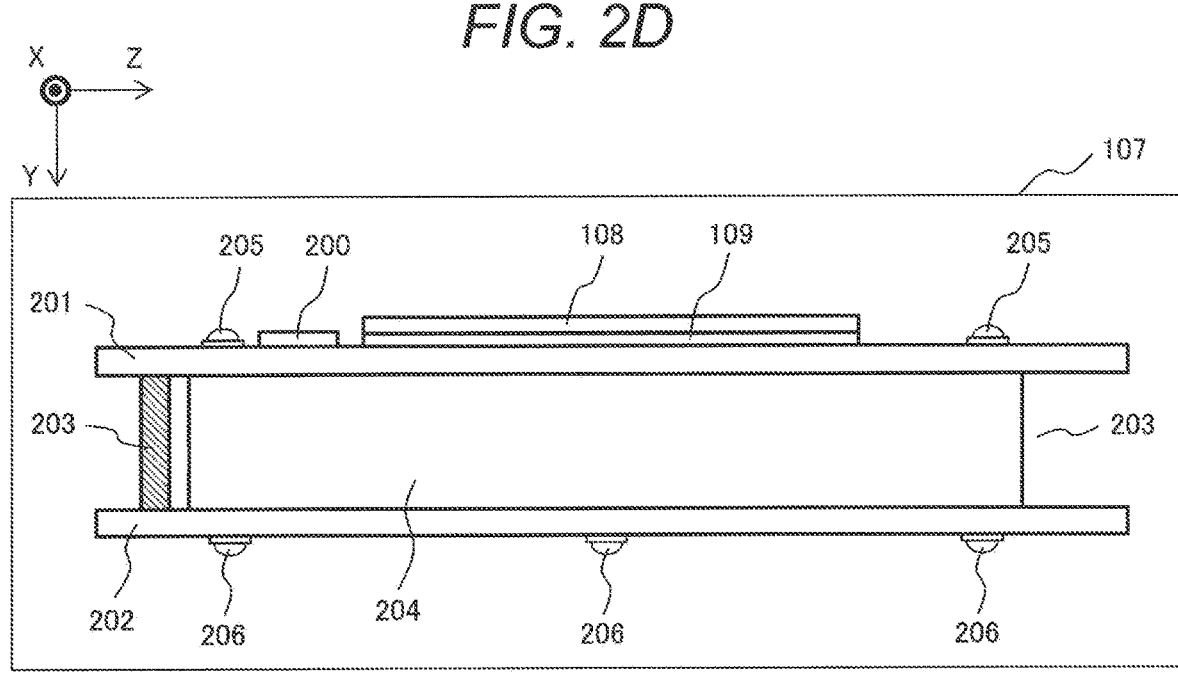
FIG. 2D is a diagram illustrating one example of the configuration of the radiation detector module according to the first embodiment.
Figure 2E:
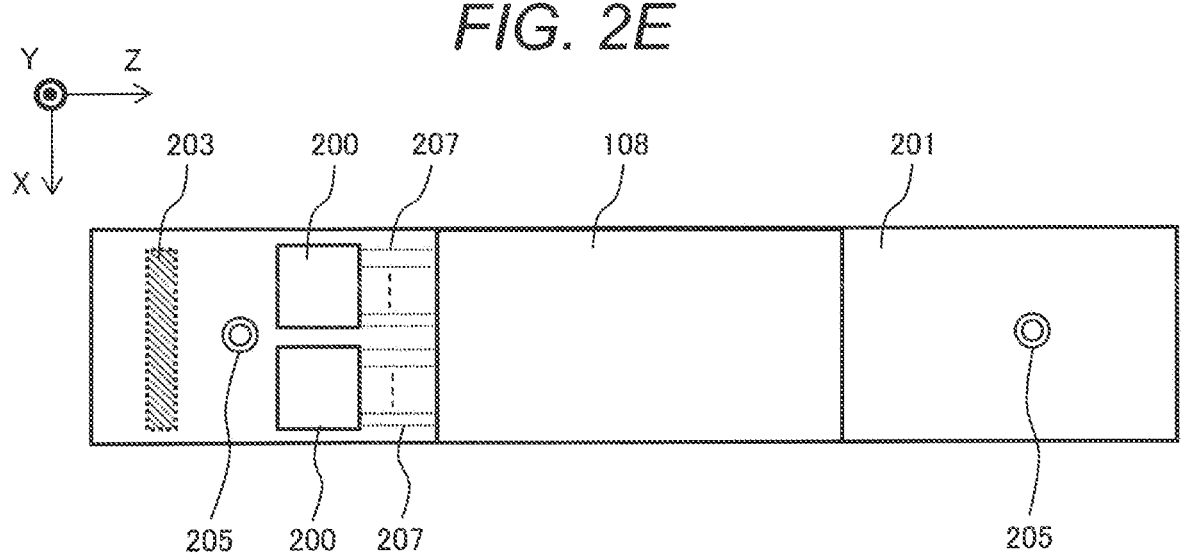
FIG. 2E is a diagram illustrating one example of the configuration of the radiation detector module according to the first embodiment.

However, as illustrated in FIG. 2D and FIG. 2E, in a case where the analog signals 207 which are output from the photodiode 109 are taken out from one side in the body-axis direction (the Z-axis direction), the AD conversion chips 200 on the detector substrate 201 and the stacking connector 203 which connects the detector substrate 201 with the control substrate 202 are disposed on one side in the body-axis direction (the Z-axis direction) without being dividedly disposed.

Figure 3A:
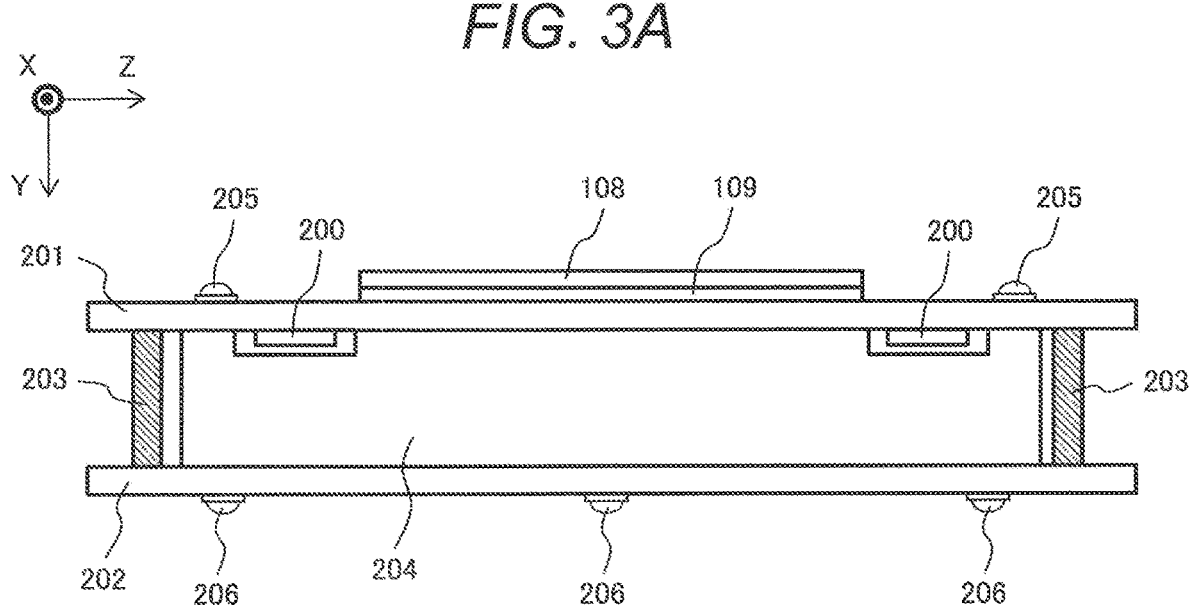
FIG. 3A is a diagram illustrating one example of the radiation detector module according to one modification of the first embodiment.

FIG. 3A illustrates one example that the AD conversion chips 200 are disposed on a rear face of the detector substrate 201. Incidentally, in the configuration in FIG. 3A, a front face of the detector substrate 201 is a face on which the photodiode 109 is disposed. In this case, the analog electric signals 207 which are output from the photodiode 109 are drawn out to the rear face of the detector substrate 201 and are sent to the conversion chips 200.

Figure 3B:
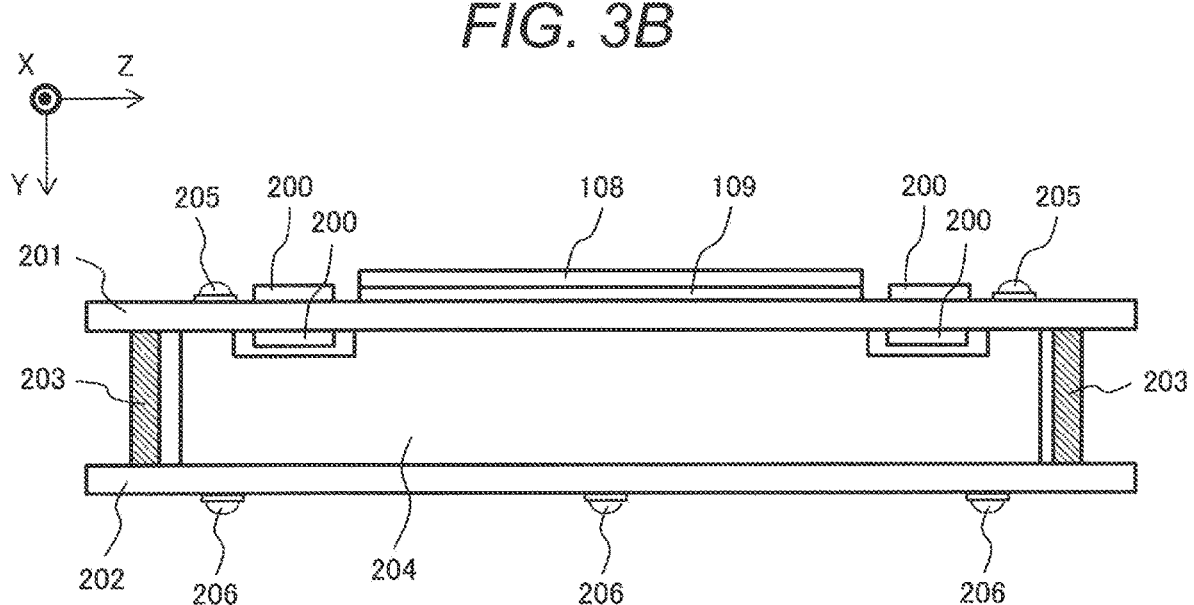
FIG. 3B is a diagram illustrating one example of the radiation detector module according to one modification of the first embodiment.

In addition, as illustrated in FIG. 3B, the AD conversion chips 200 may be disposed on both the rear face and the front face of the detector substrate 201. Owing to disposition of the AD conversion chips 200 on both the front face and the rear face of the detector substrate 201, it becomes possible to cope with an increase in the number of channels of the photodiode 109 caused by an increase in row number and so forth. Also, in this case, the respective elements may be disposed in the Z-axis direction in the order of the fixing screw 205—the AD conversion chip 200—the photodiode 109—the AD conversion chip 200—the fixing screw 205 and may also be disposed in the order of the AD conversion chip 200—the fixing screw 205—the photodiode 109—the fixing screw 205—the AD conversion chip 200.

Figure 4A:
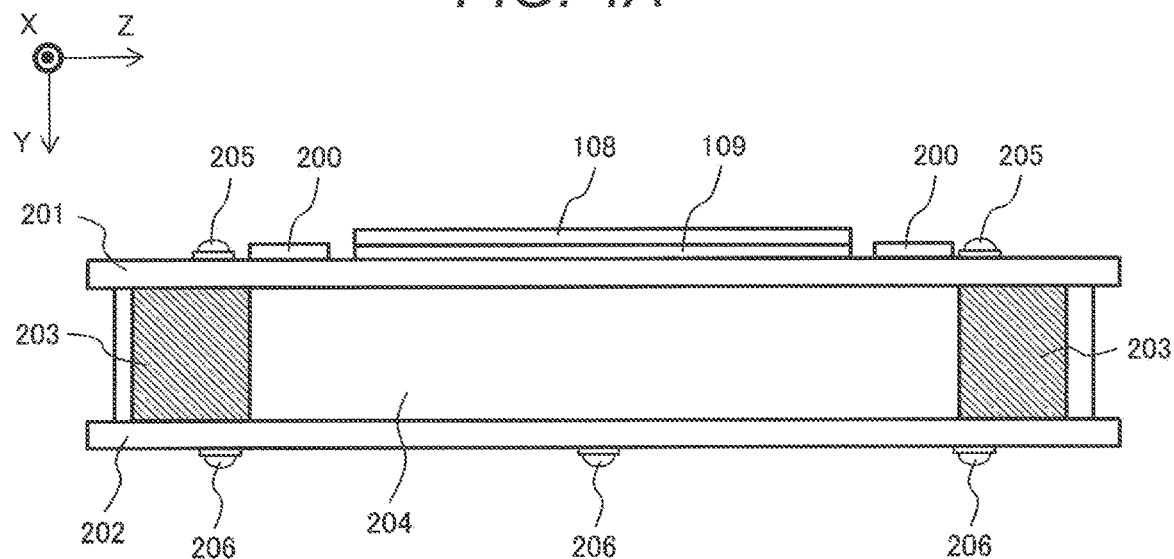
FIG. 4A is a diagram illustrating one example of the radiation detector module according to one modification of the first embodiment.
Figure 4B:
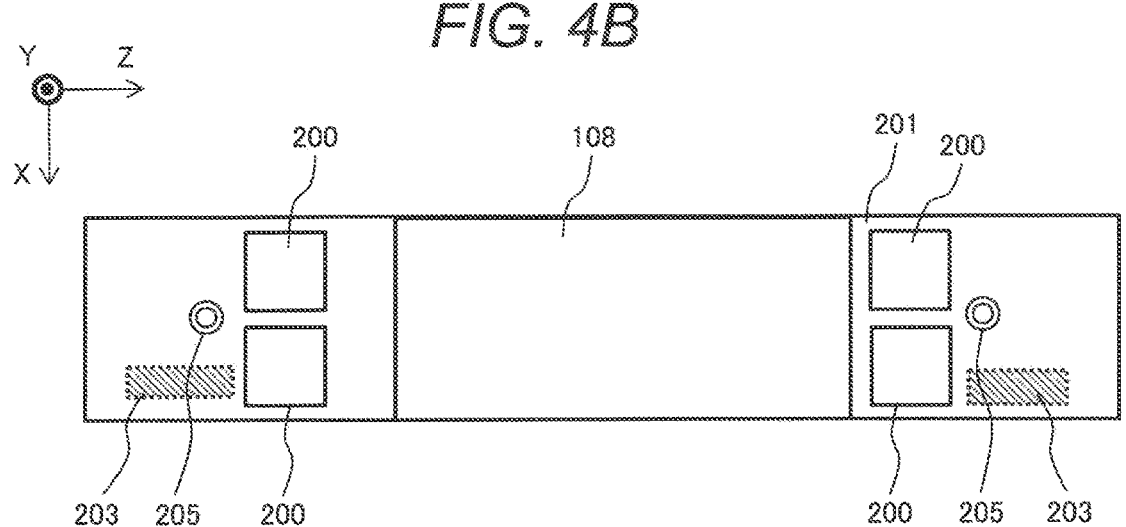
FIG. 4B is a diagram illustrating one example of the radiation detector module according to one modification of the first embodiment.
Figure 4C:
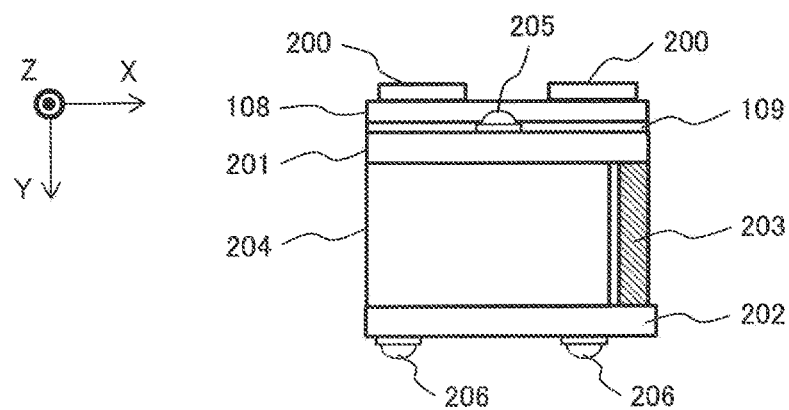
FIG. 4C is a diagram illustrating one example of the radiation detector module according to one modification of the first embodiment.
Figure 5A:
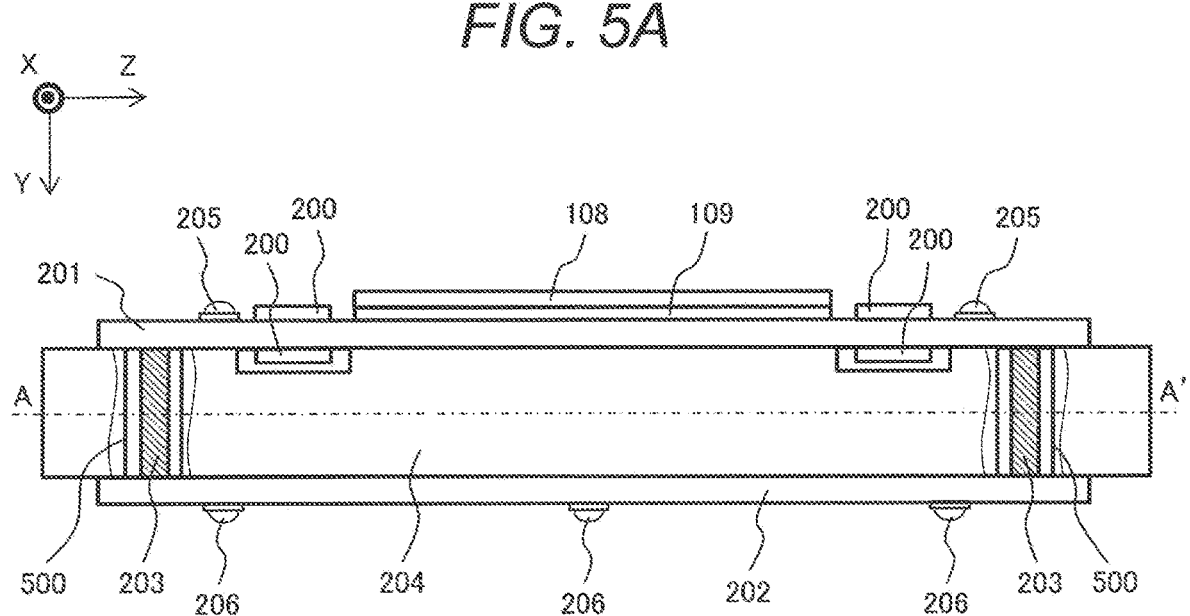
FIG. 5A is a diagram illustrating one example of the radiation detector module according to one modification of the first embodiment.
Figure 5B:
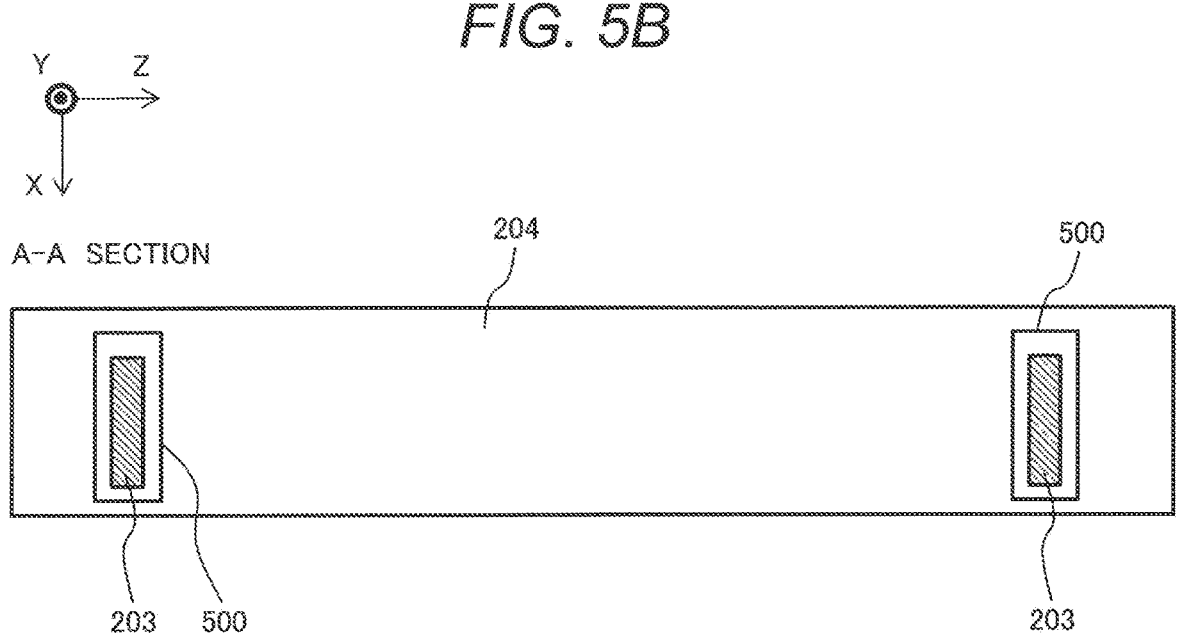
FIG. 5B is a diagram illustrating one example of the radiation detector module according to one modification of the first embodiment.
Figure 5C:
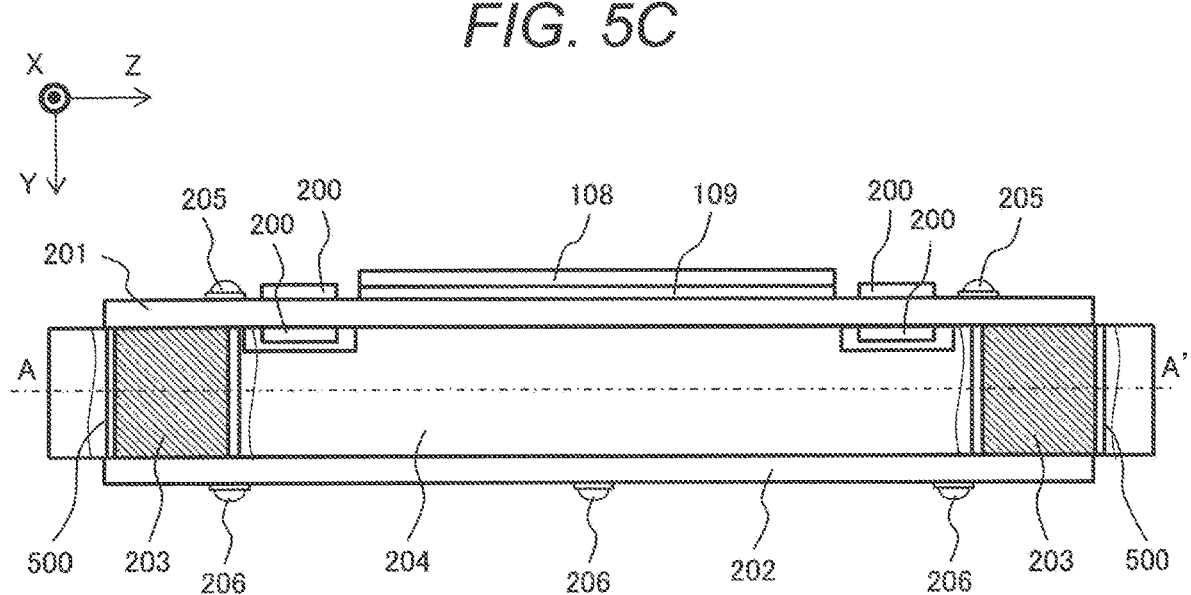
FIG. 5C is a diagram illustrating one example of the radiation detector module according to one modification of the first embodiment.
Figure 5D:
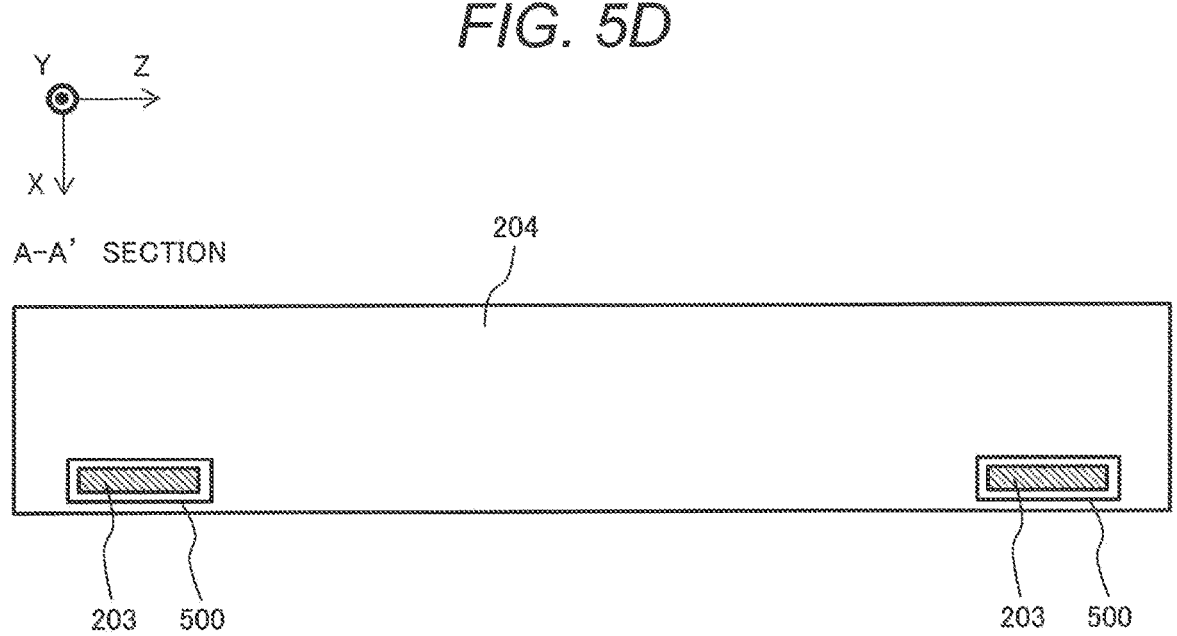
FIG. 5D is a diagram illustrating one example of the radiation detector module according to one modification of the first embodiment.

In addition, the orientation of each stacking connector 203 may be changed. Examples that the orientation of each stacking connector 203 is changed are illustrated in FIG. 4A, FIG. 4B, and FIG. 4C. Also, the shape of the support structure 204 is changed in association with orientation changing of each stacking connector 203. Also, in this case, the respective elements may be disposed in the Z-axis direction in the order of the fixing screw 205—the AD conversion chip 200—the photodiode 109—the AD conversion chip 200—the fixing screw 205 and may also be disposed in the order of the AD conversion chip 200—the fixing screw 205—the photodiode 109—the fixing screw 205—the AD conversion chip 200.

In addition, as illustrated in FIG. 5A to FIG. 5D, it is also possible to form through-holes 500 through which the stacking connectors 203 pass in the support structure 204. A contact area between the detector substrate 201 and the support structure 204 and a contact area between the control substrate 203 and the support structure 204 are increased by passing the stacking connectors 203 through the through-holes 500 and thereby it becomes possible to more increase the rigidity of the both substrates 201 and 203. Also, in this case, the respective elements may be disposed in the Z-axis direction in the order of the fixing screw 205—the AD conversion chip 200—the photodiode 109—the AD conversion chip 200—the fixing screw 205 and may also be disposed in the order of the AD conversion chip 200, the fixing screw 205—the photodiode 109—the fixing screw 205—the AD conversion chip 200.

Second Embodiment

In the radiation detector module 107 according to the second embodiment of the present invention, floating connectors are used as the stacking connectors 203 which connect the detector substrate 201 with the control substrate 202 in the first embodiment. A resin substrate is used as the control substrate 202. On the other hand, since densification of the wiring and flatness of a surface on which the photodiode 109 is loaded are requested with an increase of the row number, a ceramics substrate is used as the detector substrate 201. However, the ceramics substrate is large in tolerance and therefore it is preferable to absorb the tolerance.

The radiation detector module 107 according to the second embodiment will be described by using FIG. 6A to FIG. 6C. Since the wiring is more densified with an increase of the row number, the ceramics substrate is used as the detector substrate 201. However, the ceramics substrate is large in tolerance and therefore it is preferable to absorb the tolerance as described above.

Figure 6A:
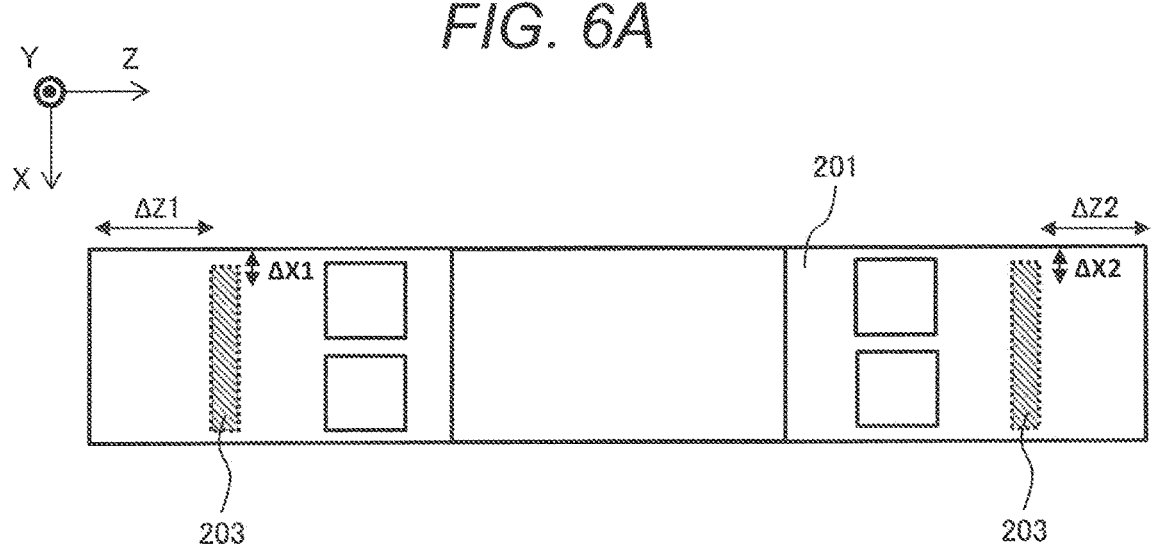
FIG. 6A is a diagram illustrating one example of a configuration of a radiation detector module according to a second embodiment of the present invention, that is, the diagram illustrating one example of a position tolerance of each stacking connector on the detector substrate.
Figure 6B:
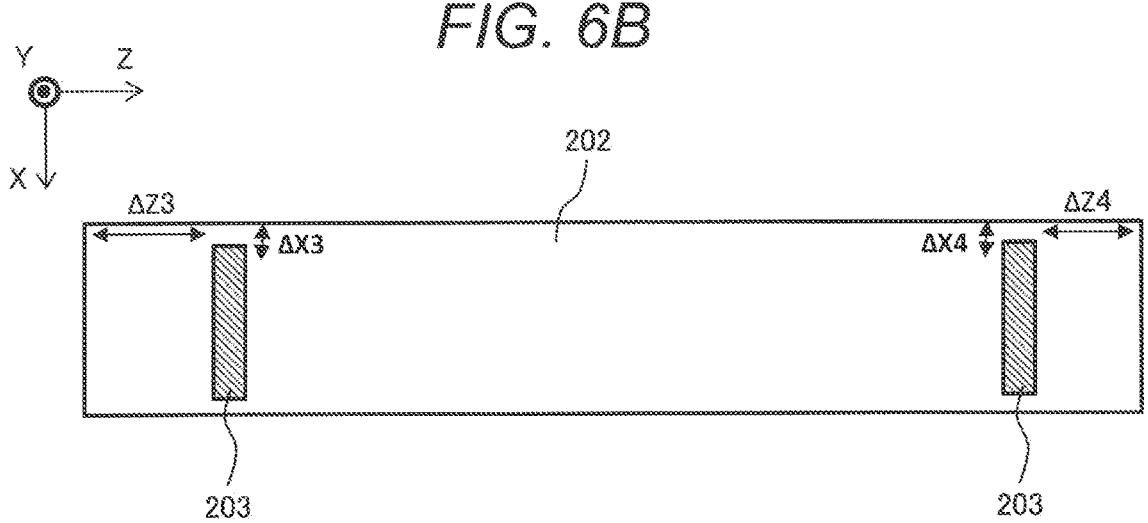
FIG. 6B is a diagram illustrating one example of the position tolerance of each stacking connector on the control substrate in the second embodiment.

As illustrated in FIG. 6A and FIG. 6B, positional tolerances ($\Delta X1$, $\Delta Z1$) and ($\Delta X2$, $\Delta Z2$) of the stacking connectors 203 which are mounted on the detector substrate 201 and positional tolerances ($\Delta X3$, $\Delta Z3$) and ($\Delta X4$, $\Delta Z4$) of the stacking connectors 203 which are mounted on the control substrate 202 occur.

Figure 6C:
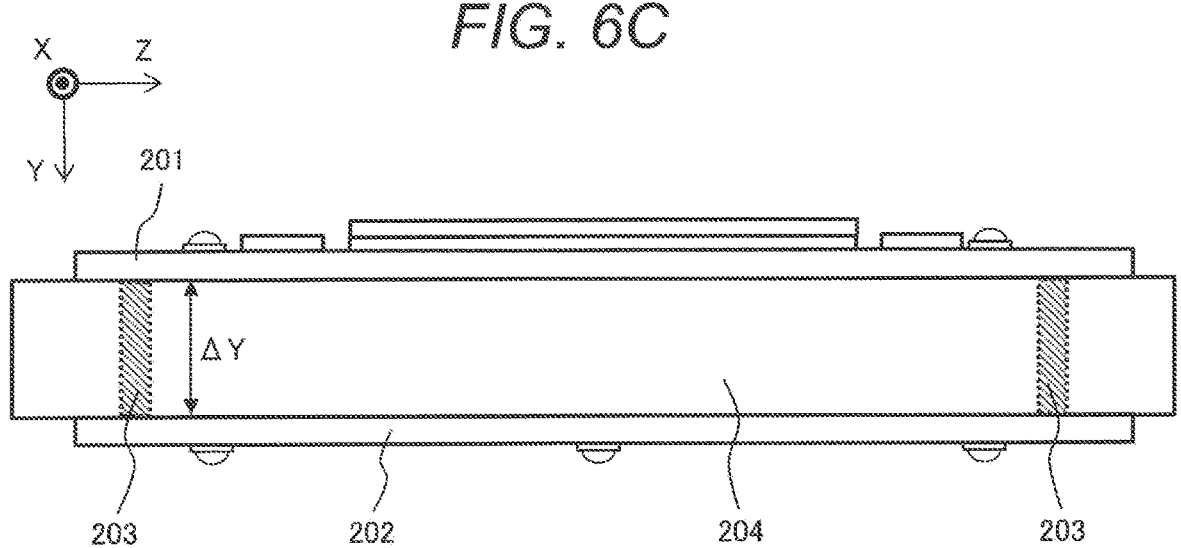
FIG. 6C is a diagram illustrating one example of a height tolerance of the support structure in the second embodiment.

In addition, as illustrated in FIG. 6C, a height tolerance ($\Delta Y$) of the support structure 204 occurs, and cumulative tolerances reach ($\Delta X1+\Delta X3$, $\Delta Y$, $\Delta Z1+\Delta Z3$) and ($\Delta X2+\Delta X4$, $\Delta Y$, $\Delta Z2+\Delta Z4$). In a case where these values are increased, a contact failure may occur in each stacking connector 203. Accordingly, in the second embodiment, the above cumulative tolerances are absorbed by using the floating connectors as the stacking connectors 203 for connecting the detector substrate 201 with the control substrate 202 and thereby it becomes possible to reduce stress which would be imparted when the stacking connectors 203 are fitted into the support structure 204.

Third Embodiment

The third embodiment pertains to an X-ray shield structure for the radiation detector module 107. In the radiation detector module 107, it is preferable to dispose X-ray sensor units in an X-ray irradiation field 700 and, on the other hand, it is preferable to avoid failures of electric components which are caused by being irradiated with the X-rays. Accordingly, as illustrated in FIG. 7, in the third embodiment, the scintillator 108 and the photodiode 109 which are disposed on the detector substrate 201 as the X-ray sensor units are disposed in the X-ray irradiation field 700 and the stacking connectors 203 and the AD conversion chips 200 are disposed outside the X-ray irradiation field 700. Thereby, it becomes possible to avoid the failures of the electric components which are caused by being directly irradiated with the X-rays.

Figure 8A:
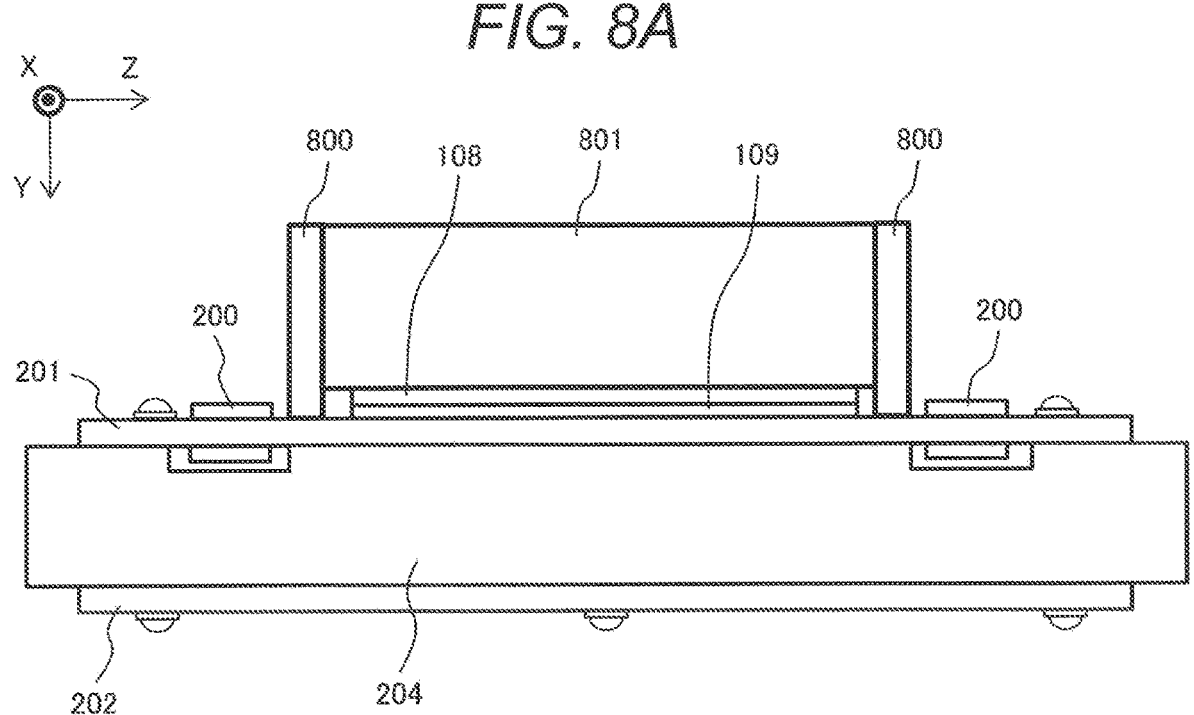
FIG. 8A is a diagram illustrating one example that the X-ray shields support a collimator plate in the third embodiment.
Figure 8B:
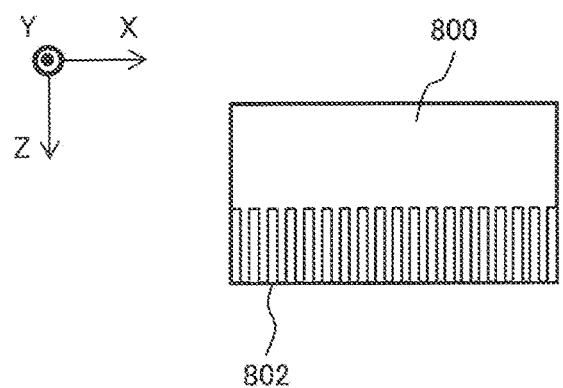
FIG. 8B is a diagram illustrating one example that grooves for supporting the collimator plate are formed in each X-ray shield in the third embodiment.

In addition, it is also preferable to shield also X-rays which are scattered from the subject 106 to the respective electric components. FIG. 8A illustrates one example that each X-ray shield 800 is disposed between the photodiode 109 and each AD conversion chip 200 so as to prevent the AD conversion chips 200 from being irradiated with the scattered X-rays. FIG. 8B illustrates one example that a plurality of grooves 802 which are adapted to support a collimator plate 801 are formed in the X-ray shield 800. Here, the X-ray shield 800 has the plurality of grooves 802 which are adapted to support the collimator plate 801 which is disposed on the scintillator 108 along a channel direction (an X-axis direction) in order to reduce crosstalk which is induced with the scattered rays. Accordingly, a metal such as brass and so forth which is low in X-ray transmissivity and is machined with ease is used as the material of the X-ray shield 800.

Figure 9:
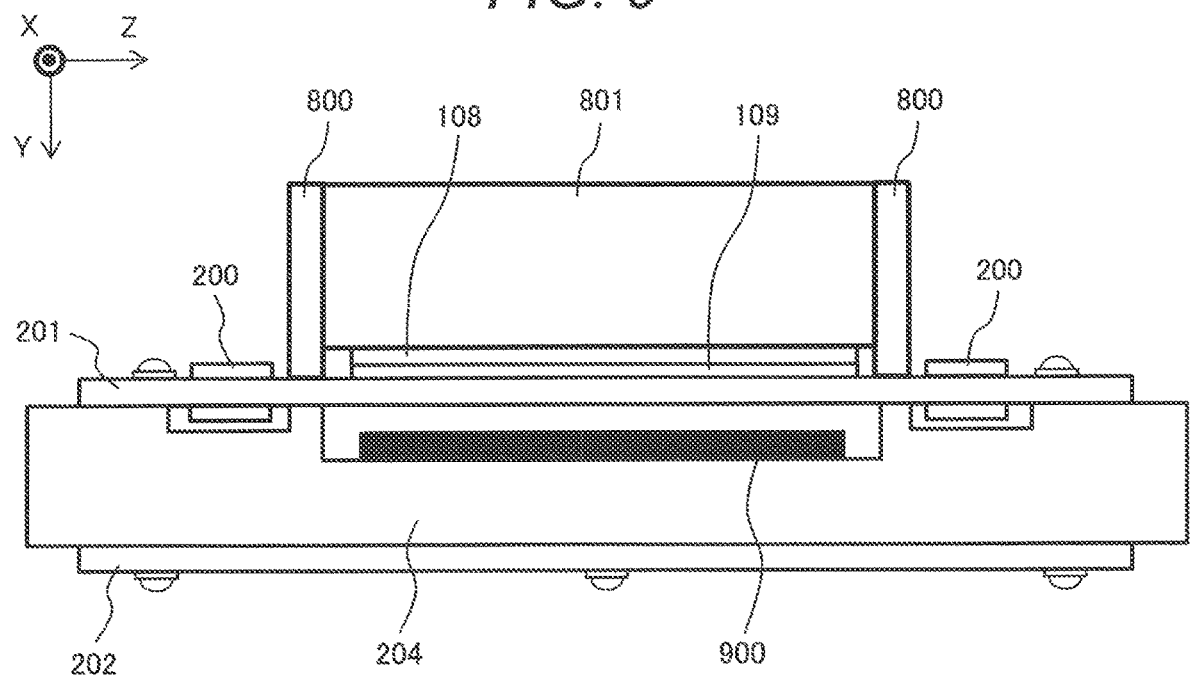
FIG. 9 is a diagram illustrating one example that another X-ray shield is disposed between the detector substrate and the control substrate.

Further, it is also preferable to prevent the control substrate 204 from being irradiated with the X-rays which are transmitted without being absorbed by the scintillator 108 on the detector substrate 201. Accordingly, FIG. 9 illustrates one example that an X-ray shield 900 is disposed on the support structure 204 which is disposed between the detector substrate 201 and the control substrate 204. Thereby, it becomes possible to avoid the failures of the control substrate 202 which are caused by irradiation with the transmitted X-rays.

Fourth Embodiment

Figure 10A:
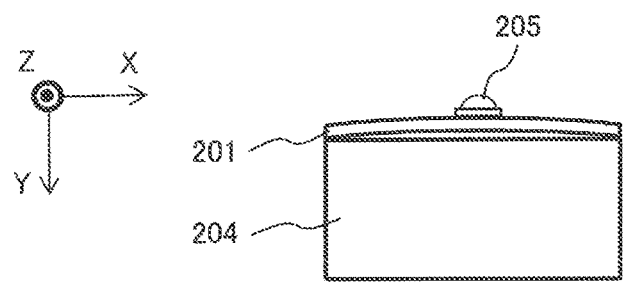
FIG. 10A is a diagram illustrating one example that the detector substrate and the support structure are fixed together in the radiation detector module according to a fourth embodiment.
Figure 10B:
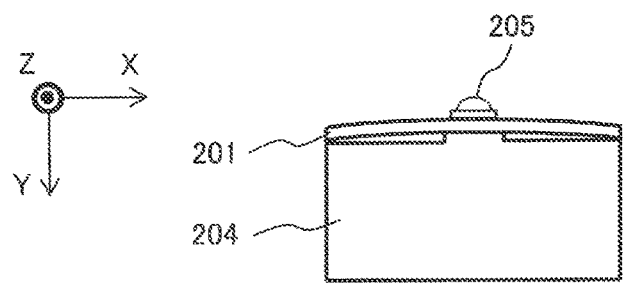
FIG. 10B is a diagram illustrating one example that the detector substrate and the support structure are fixed together in the fourth embodiment.

In the fourth embodiment, a structure that the detector substrate 201, the support structure 204, and the X-ray shield 800 are attached and a procedure of attaching the substrates 201 and 204 and the X-ray shield will be described. First, the detector substrate 201 and the support structure 204 are attached together. Since densification of the wiring and flatness of the surface on which the photodiode 109 is loaded are requested to the detector substrate 201 with an increase of the row number, the ceramics substrate is used as the detector substrate 201. However, the ceramics substrate is hard and has such a feature that it is easy to break. Here, as illustrated in FIG. 10A, in a case where the detector substrate 201 is warped and attachment surfaces of the detector substrate 201 and the support structure 204 are mutually different in flatness, when the detector substrate 201 and the support structure 204 are fixed with the fixing screw 205, the ceramics detector substrate 201 may be broken. Accordingly, as illustrated in FIG. 10B, it becomes possible to prevent breakage of the detector substrate 201 by reducing a contact area between the detector substrate 201 and the support structure 204 even in a case where the detector substrate 201 is warped.

Figure 11A:
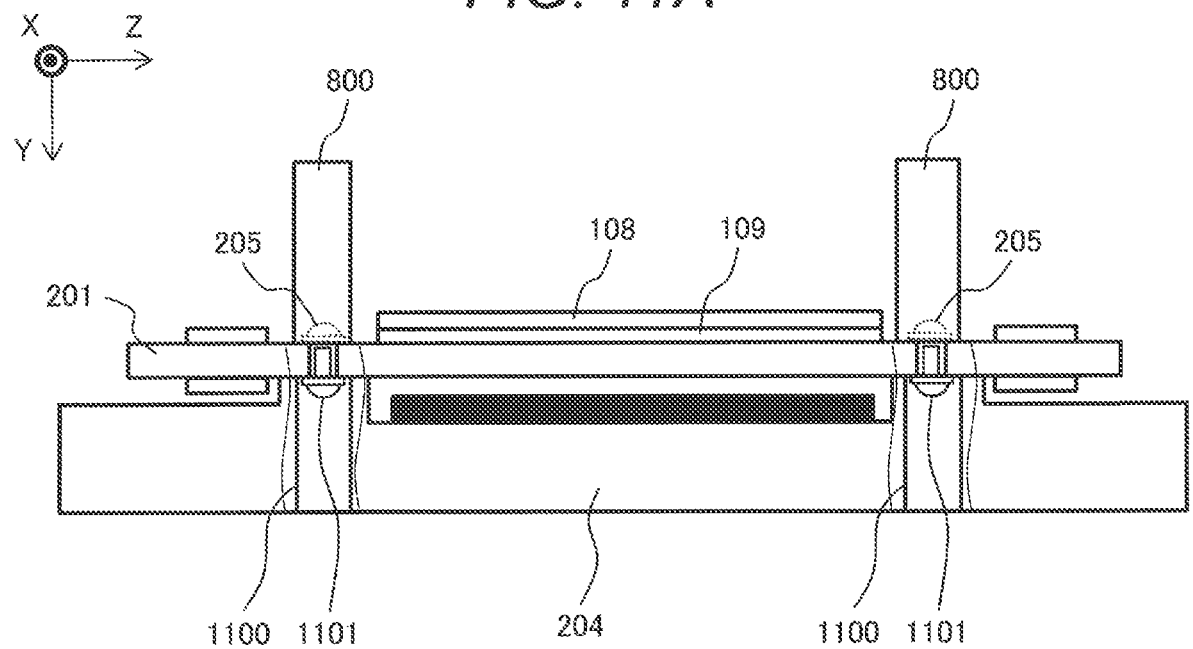
FIG. 11A is a diagram illustrating one example that the detector substrate and the X-ray shield are fixed together in the fourth embodiment.
Figure 11B:
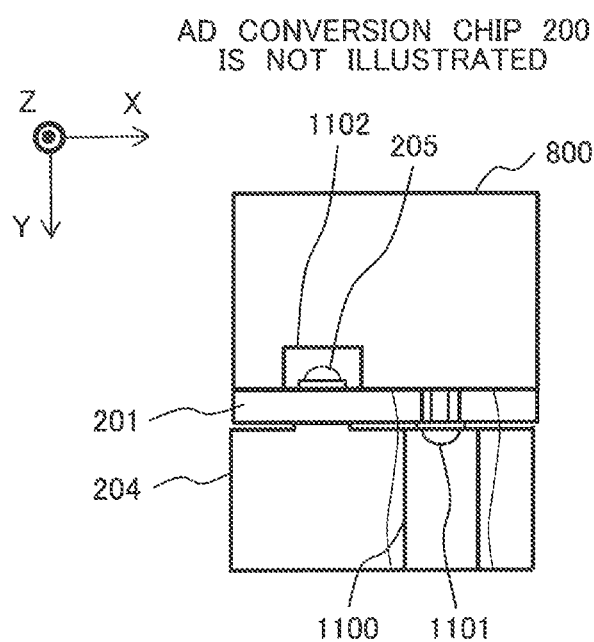
FIG. 11B is a diagram illustrating one example that the detector substrate and the X-ray shield are fixed together in the fourth embodiment.
Figure 11C:
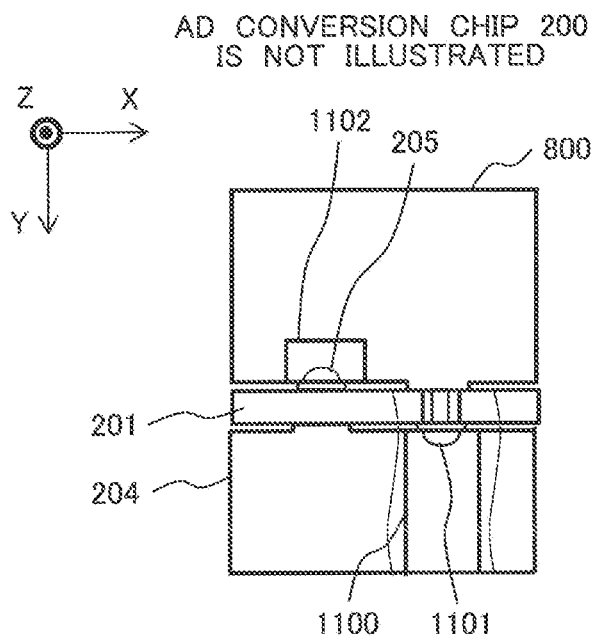
FIG. 11C is a diagram illustrating one example that the detector substrate and the X-ray shield are fixed together in the fourth embodiment.
Figure 11D:
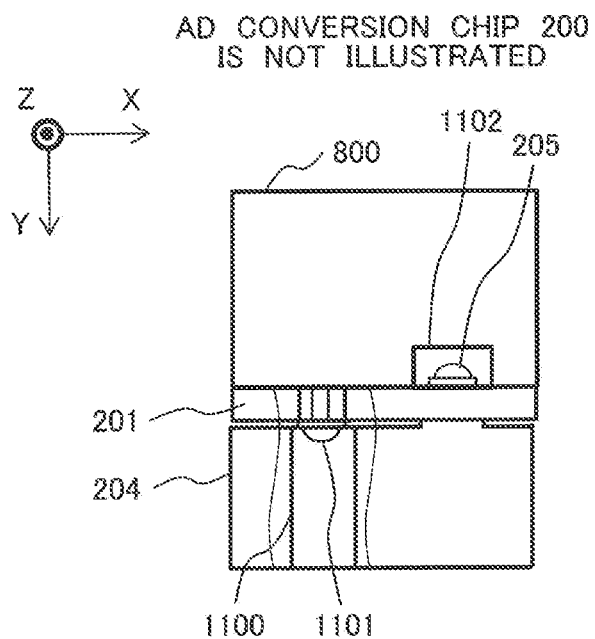
FIG. 11D is a diagram illustrating one example that the detector substrate and the X-ray shield are fixed together in the fourth embodiment.
Figure 11E:
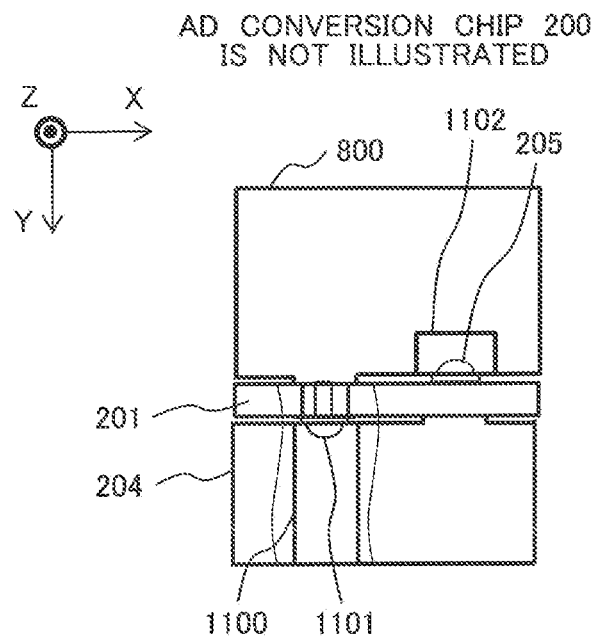
FIG. 11E is a diagram illustrating one example that the detector substrate and the X-ray shield are fixed together in the fourth embodiment.
Figure 12:
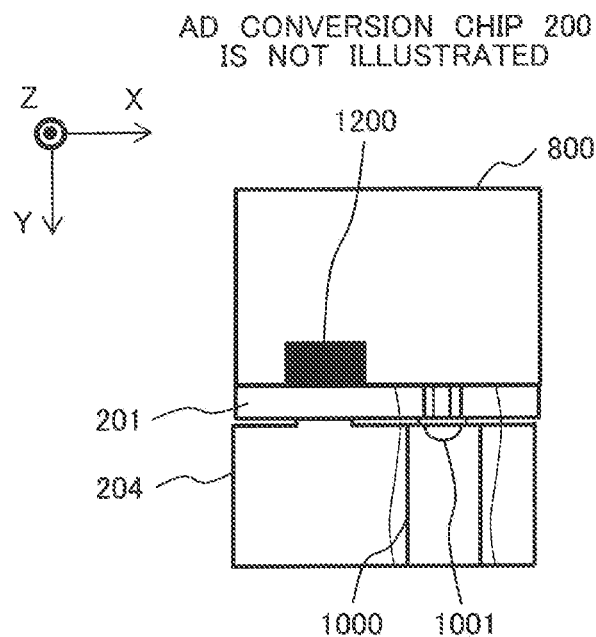
FIG. 12 is a diagram illustrating one example that a curing type X-ray shield is embedded into a back facing hole in the X-ray shield in the fourth embodiment.

Then, the X-ray shields 800 are attached to the detector substrate 201. FIG. 11A illustrates one example that the detector substrate 201, the support structure 204, and the X-ray shields 800 are assembled together while suppressing the length of the detector substrate 201 in the body-axis direction. The support structure 204 has through-holes 1100 for fixing the X-ray shields 800, and the X-ray shields 800 are fixed to the detector substrate 201 from the rear face side of the support structure 204 by using fixing screws 1101. Since the X-ray shields 800 are fixed to the detector substrate 201 from the rear face side of the support structure 204, the detector substrate 201, the support structure 204, and the X-ray shields 800 are assembled together before attaching the control substrate 202. Here, since the length in the body-axis direction (the Z-axis direction) is suppressed, a position where the detector substrate 201 and the support structure 204 are fixed together with each fixing screw 205 and a position where the detector substrate 201 and each X-ray shield 800 are fixed together with each fixing screw 1101 become the same as each other in the body-axis direction (the Z-axis direction). Therefore, as illustrated in FIG. 11B, each X-ray shield 800 has a back facing hole 1102 for avoiding interference with each fixing screw 205. As illustrated in FIG. 11C, the contact area between the detector substrate 201 and each X-ray shield 800 may be reduced to the greatest possible extent for avoidance of breakage of the detector substrate 201 as described above. The shape of each X-ray shield 800 is changed in association with contact area reduction. In addition, as illustrated in FIG. 11D and FIG. 11E, the position where the detector substrate 201 and the support structure 204 are fixed together with each fixing screw 205 and the position where the detector substrate 201 and each X-ray shield 800 are fixed together with each fixing screw 1101 may be reversed in the X-axis direction. Further, as for two positions which are symmetrically disposed in the body-axis direction (the Z-axis direction), that is, the position where the detector substrate 201 and one X-ray shield 800 are fixed together and the position where the detector substrate 201 and the other X-ray shield 800 are fixed together, the positions which are illustrated in FIG. 11B to FIG. 11E may be present in the mixed state. In addition, as illustrated in FIG. 12, it becomes possible to shield the X-rays which are scattered to each AD conversion chip 200 by embedding a curing type X-ray shield 1200 into the back facing hole 1102 which is formed in each X-ray shield 800 for avoiding interference with each fixing screw 205. Here, as the curing-type X-ray shield, a shield that powder of tungsten and so forth is mixed in an adhesive is used.

Fifth Embodiment

Figure 13:
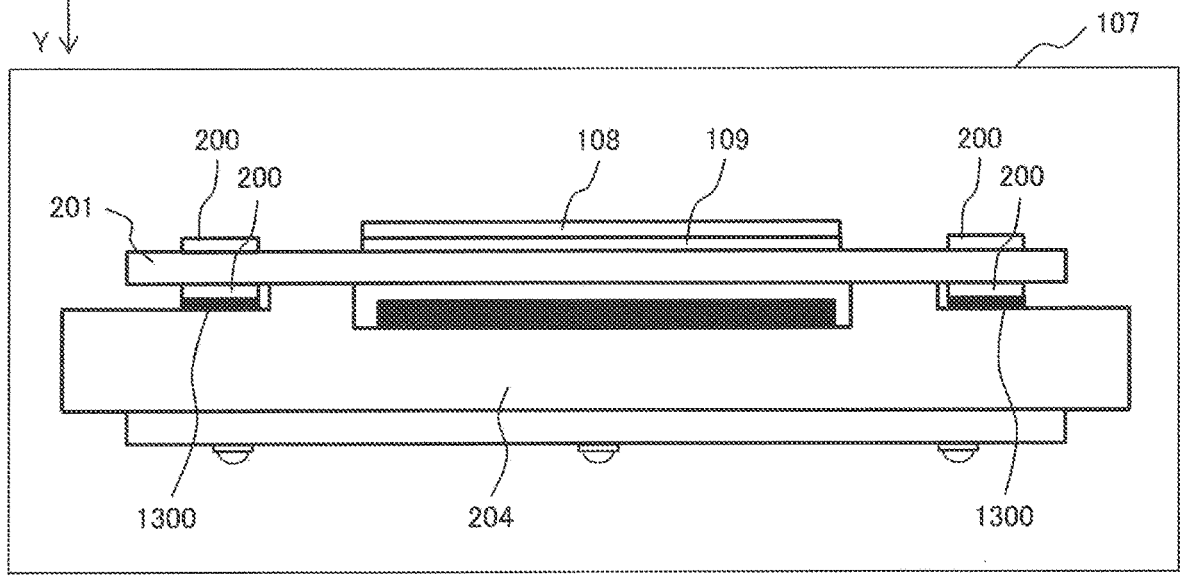
FIG. 13 is a diagram illustrating one example that the support structure and each AD conversion chip are coupled together via a heat conduction material in the radiation detector module according to a fifth embodiment of the present invention.

In the fifth embodiment, a structure of the radiation detector module 107 and a structure of the radiation detector 101 will be described from the viewpoint of heat radiation from the AD conversion chips 200. As illustrated in FIG. 13, the AD conversion chips 200 which are attached to the rear face of the detector substrate 201 are brought into thermal contact with the support structure 204 via heat conduction materials 1300 and thereby it becomes possible for the support structure 204 to absorb heat from the AD conversion chips 200 and to radiate the heat to the outside. Here, as the material of the support structure 204, a metal such as aluminum and so forth which has not only such a mechanical feature that the rigidity is high, but also such a feature that the thermal conductivity is high is used.

Figure 14:
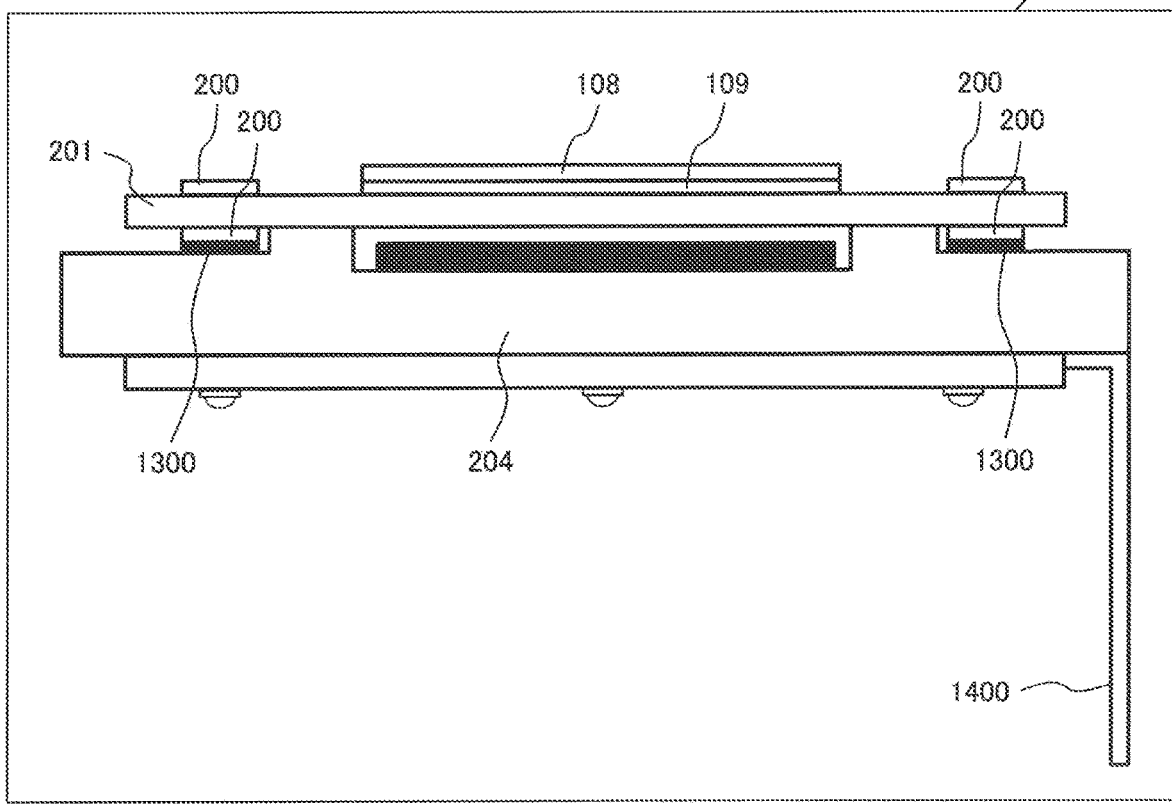
FIG. 14 is a diagram illustrating one example that a heat sink is coupled to the support structure in the fifth embodiment.

Further, as illustrated in FIG. 14, it is also possible to couple a heat sink 1400 to the support structure 204. It becomes possible to radiate the heat that the support structure 204 absorbs to the outside more effectively by not only increasing the heat capacity but also coupling the heat sink 1400 which is large in surface area to the support structure 204.

Figure 15A:
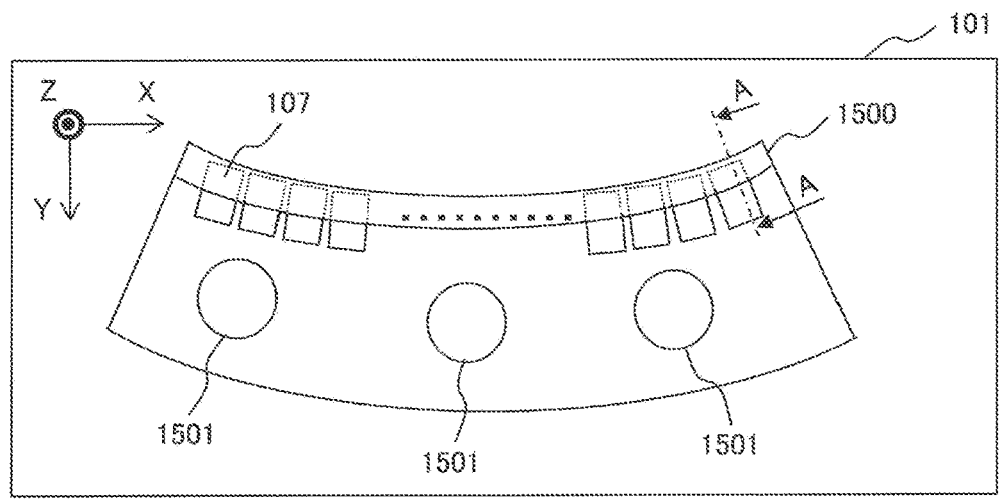
FIG. 15A is a diagram illustrating one example of a radiation detector which is configured by the radiation detector modules according to the fifth embodiment, a detector housing unit, and a cooling fan.
Figure 15B:
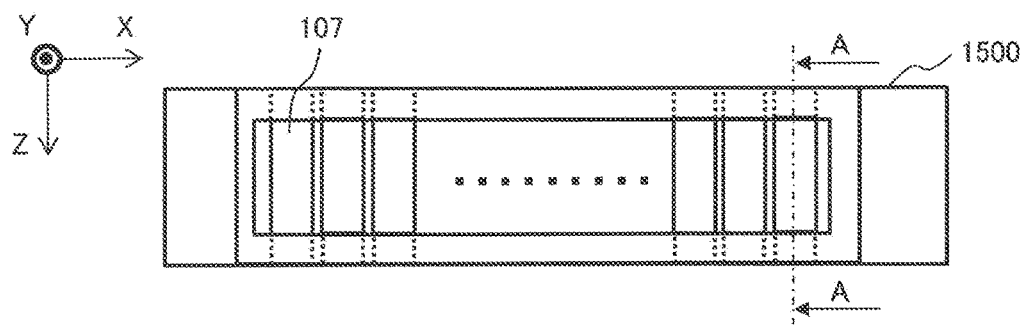
FIG. 15B is a diagram illustrating one example of the detector housing unit and the support structure according to the fifth embodiment fixed together.
Figure 15C:
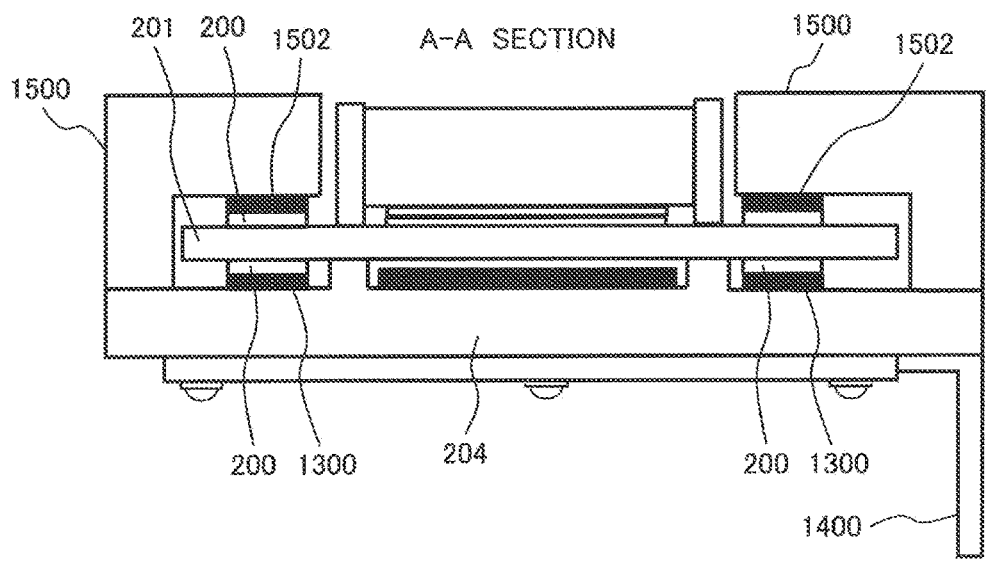
FIG. 15C is a diagram illustrating one example of the detector housing unit and the support structure according to the fifth embodiment fixed together.

In addition, as illustrated in FIG. 15A to FIG. 15C, in the radiation detector 101, the plurality of the radiation detector modules 107 are attached to a detector housing unit 1500. Here, the support structure 204 serves as an attachment face of the radiation detector module 107 to the detector housing unit 1500. It becomes possible to more heighten the heat radiation effect of the AD conversion chips 200 by fixing the support structure 204 which absorbs heat which is generated from the AD conversion chips 200 which are disposed on the detector substrate 201 to the detector housing unit 1500 which is controlled in temperature. Further, it is also possible to cool the AD conversion chips 200 by coupling the AD conversion chips 200 which are disposed on a front face of the detector substrate 201 directly to the detector housing unit 1500 via heat conduction materials 1502. In addition, it becomes possible to cool the AD conversion chips 200 which are disposed on the detector substrate 201 by attaching a plurality of fans 1501 to the detector housing unit 1500 and cooling the detector housing unit 1500, the support structure 204 and the heat sink 1400 by the fans 1501. Here, a cooling method to be adopted may be not an air-cooling method but a water-cooling method.

The present invention is not limited to the above-described embodiments, and further various modifications are included. For example, the above embodiments are described in detail for ready understanding of the present invention and are not necessarily limited to those which include all the above-described configurations. In addition, it is possible to replace part of a configuration of one embodiment with a configuration of another embodiment and it is also possible to add a configuration of another embodiment to a configuration of one embodiment. In addition, it is also possible to add/delete/replace a configuration which is included in another embodiment to/from/ with part of a configuration of each embodiment.

REFERENCE SIGNS LIST

100 . . . X-ray source
101 . . . radiation detector
102 . . . signal processing unit
103 . . . image generation unit
104 . . . turntable
105 . . . bed
106 . . . subject
107 . . . radiation detector
108 . . . scintillator
109 . . . photodiode
110 . . . AFE
111 . . . scanner
200 . . . AD conversion chip
202 . . . control substrate
203 . . . stacking connector
201 . . . detector substrate
202 . . . control substrate
203 . . . stacking connector
204 . . . support structure
205, 1101 . . . fixing screw
206 . . . screw
207 . . . analog signal
500, 1100 . . . through-hole
800, 900 . . . X-ray shield
801 . . . collimator plate
802 . . . groove

What is claimed is:

1. A radiation detector module comprising:
a detector substrate on which a scintillator, which converts X-rays which are incident upon the scintillator from a front-face side to light, a photodiode, which converts the light which is converted from the X-rays to an analog signal, and analog-to-digital (AD) conversion chips each of which amplifies the analog signal and converts the analog signal to a digital signal are disposed on a first surface of the detector substrate; and
a control substrate which supplies power to the detector substrate and controls the operation of an AD conversion unit (AFE) of each AD conversion chip,
wherein the two substrates are connected together by stacking connectors so as to form a two-stage structure and a support structure, which supports the detector substrate and the control substrate, the support structure being disposed between a second surface of the detector substrate, which is opposite to the first surface, and a first surface of the control substrate in a depth direction,
wherein the stacking connectors are disposed between the second surface of the detector substrate and the first surface of the control substrate, the stacking connectors including a first stacking connector and a second stacking connector,
wherein the AD conversion chips include a first AD conversion chip and a second AD conversion chip, the first AD conversion chip is disposed between the first stacking connector and the scintillator in a direction orthogonal to the depth direction in a plan view and the second AD conversion chip is disposed between the second stacking connector and the scintillator in the direction orthogonal to the depth direction in the plan view.

2. The radiation detector module according to claim 1, wherein floating connectors are used as the stacking connectors which connect the detector substrate with the control substrate.

3. The radiation detector module according to claim 2, wherein the support structure has through-holes through which the stacking connectors which connect the detector substrate with the control substrate pass.

4. The radiation detector module according to claim 3, wherein the scintillator and the photodiode are disposed in an X-ray irradiation field, and the AD conversion chips and the stacking connectors are disposed outside the X-ray irradiation field.

5. The radiation detector module according to claim 4, wherein X-ray shields are disposed between the photodiode and one AD conversion chip and between the photodiode and the other AD conversion chip, and the X-ray shields serve to attach a collimator plate for removing scattered rays.

6. The radiation detector module according to claim 5, wherein an attachment area between the detector substrate and the support structure is reduced so as to avoid breaking of the detector substrate caused by a difference in flatness between the detector substrate and the support structure.

7. The radiation detector module according to claim 6, wherein a position where the detector substrate and the support structure are fixed together and a position where the detector substrate and each X-ray shield are fixed together are the same in the body-axis direction.

8. The radiation detector module according to claim 7, wherein a curing-type X-ray shield is embedded into a back facing hole in each X-ray shield in order to avoid interference with a fixing screw for fixing the detector substrate and the support structure together.

9. The radiation detector module according to claim 8, wherein each AD conversion chip is coupled with the support structure via a heat conductive material.

10. The radiation detector module according to claim 9, wherein a heat sink is coupled to the support structure.

11. A radiation detector, wherein the support structure is thermally coupled to a radiation detector housing unit to which the plurality of radiation detector modules according to claim 10 are attached.

12. The radiation detector according to claim 11, wherein the AD conversion chip is coupled to the radiation detector housing unit via a heat conductive material.

13. A radiographic imaging apparatus comprising:
   a scanner which includes the radiation detector according to claim 12 therein;
   a signal processing unit which processes an output signal from the radiation detector; and
   an image generation unit which generates an image signal from the output signal processed by the signal processing unit.

14. The radiographic imaging apparatus according to claim 13, wherein the signal processing unit controls the operation of the scanner.

\* \* \* \* \*